United States Patent [19]
Williams, III et al.

[11] Patent Number: 5,413,092
[45] Date of Patent: May 9, 1995

[54] SHEATH FOR ENDOSCOPE

[75] Inventors: William B. Williams, III, Ripley, Tenn.; Dennis J. Reisdorf; William T. Donofrio, both of Jacksonville, Fla.

[73] Assignee: Xomed-Treace, Inc., Jacksonville, Fla.

[21] Appl. No.: 98,968

[22] Filed: Jul. 29, 1993

Related U.S. Application Data

[63] Continuation of Ser. No. 720,096, Jun. 24, 1991, Pat. No. 5,237,984.

[51] Int. Cl.⁶ .............................................. A61B 1/00
[52] U.S. Cl. ........................................... 128/4; 128/6
[58] Field of Search .................. 128/4, 6, 844, 7, 10

[56] References Cited

U.S. PATENT DOCUMENTS

| | | | |
|---|---|---|---|
| 2,372,171 | 3/1945 | Bennett | 359/507 X |
| 3,528,720 | 9/1970 | Treace | 359/510 |
| 3,895,155 | 7/1975 | Shukuri et al. | 359/507 X |
| 4,064,308 | 12/1977 | Laurin | 359/507 X |
| 4,353,358 | 10/1982 | Emerson | 128/4 |
| 4,522,196 | 6/1985 | Cunningham et al. | 128/4 |
| 4,610,242 | 9/1986 | Santangelo et al. | 128/4 |
| 4,646,722 | 3/1987 | Silverstein et al. | 128/4 |
| 4,721,097 | 1/1988 | D'Amelio | 128/4 |
| 4,741,326 | 5/1988 | Sidall et al. | 128/4 |
| 4,779,613 | 10/1988 | Hashiguchi et al. | 128/6 |
| 4,809,678 | 3/1989 | Klein | 128/4 |
| 4,825,850 | 5/1989 | Opie et al. | 128/4 |
| 4,878,485 | 11/1989 | Adair | 128/6 |
| 4,886,049 | 12/1989 | Darras | 128/4 |
| 4,942,867 | 7/1990 | Takahashi et al. | 128/6 |
| 4,951,677 | 8/1990 | Crowley et al. | 128/4 X |
| 4,974,580 | 12/1990 | Anapliotis | 128/4 |
| 4,991,564 | 2/1991 | Takahashi et al. | 128/4 |
| 4,991,565 | 2/1991 | Takahashi et al. | 128/4 |
| 5,050,585 | 9/1991 | Takahashi | 128/4 |
| 5,078,483 | 1/1992 | Herzberg | 359/510 |
| 5,088,178 | 2/1992 | Stolk | 128/4 X |
| 5,168,863 | 12/1992 | Kurtzer | 604/171 X |
| 5,193,525 | 3/1993 | Silverstein et al. | 128/4 |

FOREIGN PATENT DOCUMENTS

| | | | |
|---|---|---|---|
| 3508833 | 9/1986 | Germany | 128/4 |

*Primary Examiner*—Richard J. Apley
*Assistant Examiner*—Beverly A. Meindl
*Attorney, Agent, or Firm*—Gipple & Hale

[57] ABSTRACT

The sheath for endoscope includes a tubular sleeve portion and a lens cover portion at one end of the tubular sleeve portion. The lens cover portion is of a predetermined thickness that minimizes light reflection onto the field of view of the endoscope. The sheath thus provides optimum visual acuity when used with the endoscope. The lens cover portion can include an antifogging ingredient to minimize condensation or congregation of fluids during examination. In several embodiments of the invention the sheath is rigid and in other embodiments of the invention the sheath is flexible. In any of the embodiments the lens cover portion can be joined to the inside, outside or end of the tubular sleeve. The lens cover portion can be formed with a cap section that is oriented at a selected predetermined angle with respect to a central axis. The sheath can have one or more reduced diameter sections to prevent relative slippage between the sleeve and the barrel of the endoscope. The sheath can also be incorporated in a cover for covering the entire endoscope. The cover includes a drape portion that covers the main body portion of the endoscope and the sheath is detachably joinable to the drape portion or can be integrally joined thereto.

17 Claims, 5 Drawing Sheets

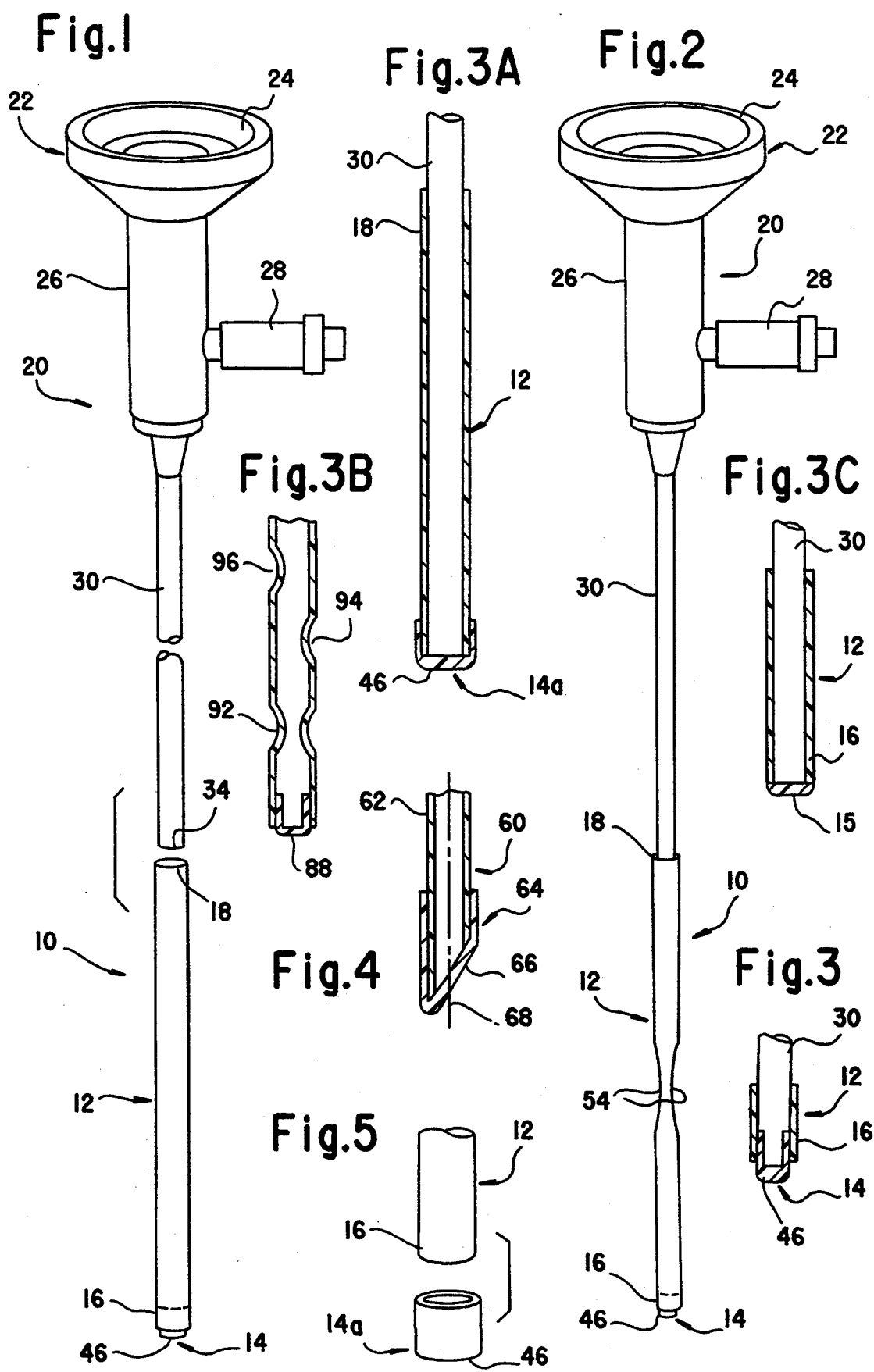

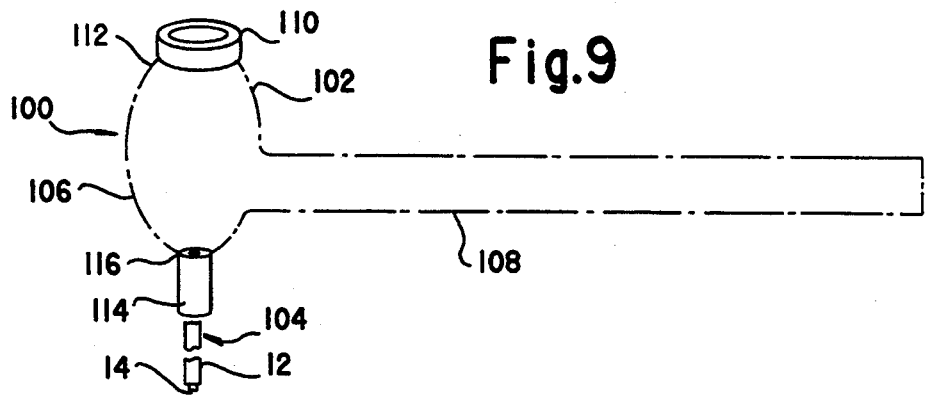
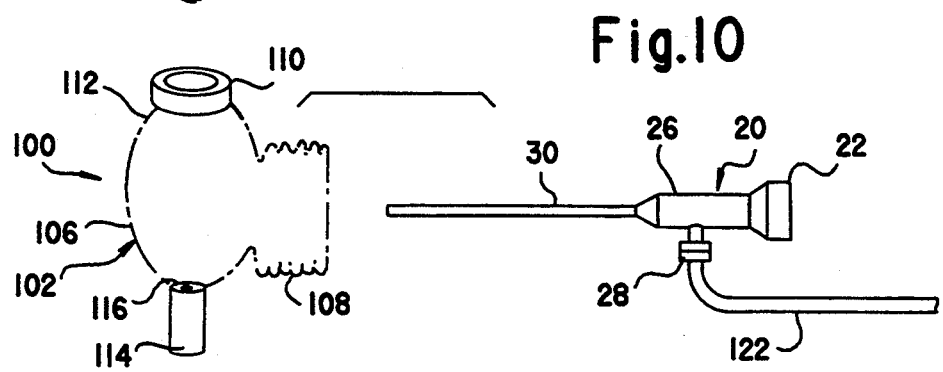
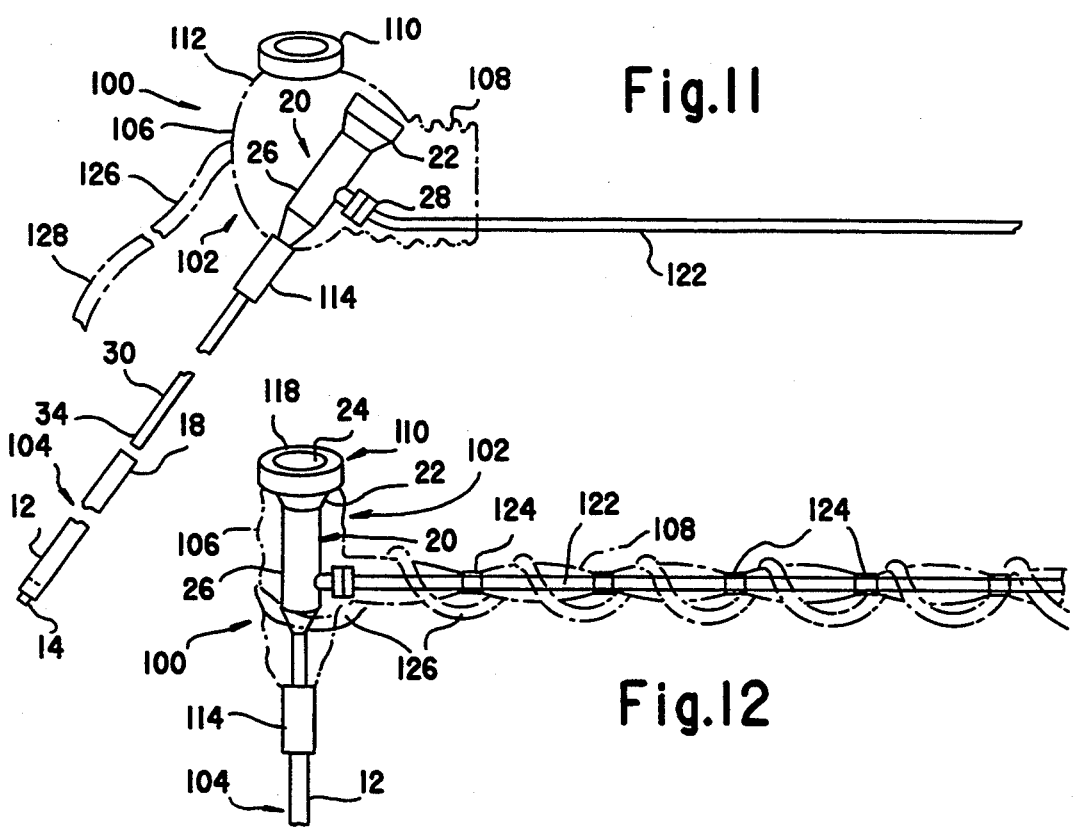

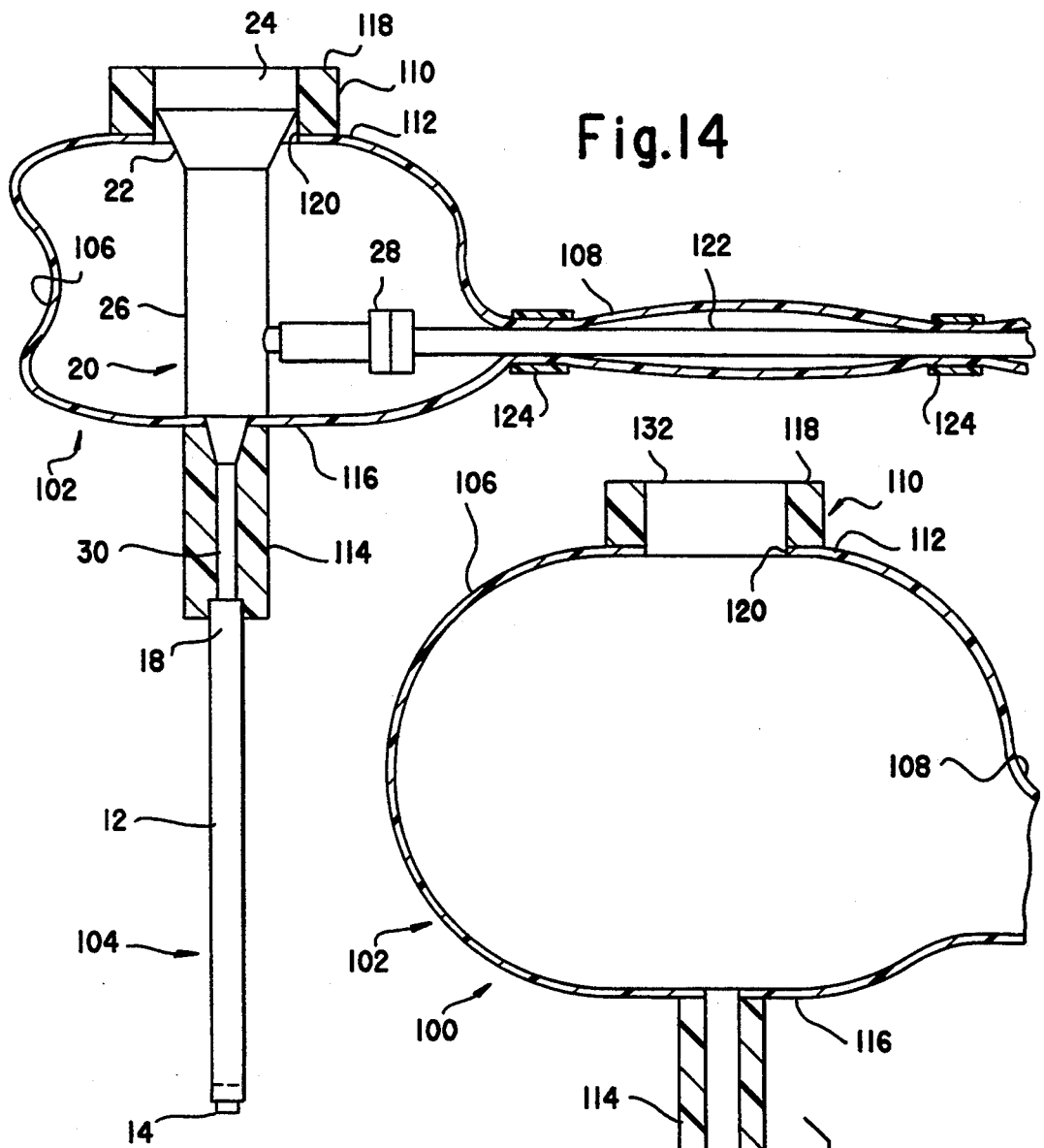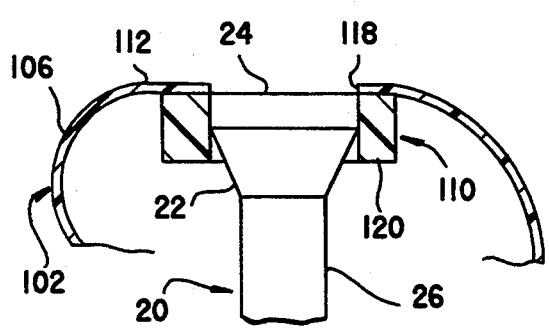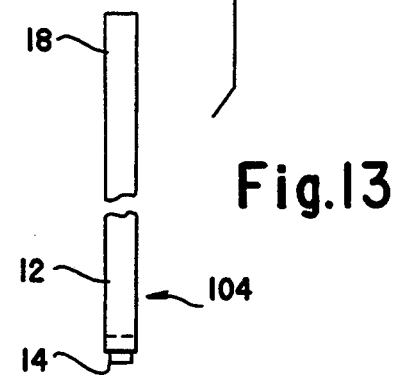

SHEATH FOR ENDOSCOPE

This is a continuation of application Ser. No. 07/720,096 filed Jun. 24, 1991, now patent No. 5,237,984.

BACKGROUND OF THE INVENTION

This invention is directed to disposable sheaths for medical examining devices that are inserted into body cavities and more particularly to a disposable sheath for use with an endoscope.

Reusable medical devices, especially those which are inserted into cavities of the body such as endoscopes, must be in a sterile condition before each use. Procedures for sterlizing reusable medical devices can be relatively time consuming and expensive. In addition, there is also a likelihood that the sterility of a reusable medical device will be compromised between the time sterilization is performed and the time the device is used, especially if there is a relatively long time lapse between sterilization and use. Furthermore, in many instances it is inconvenient to sterilize a medical device just before it will be used.

It is common practice with some known reusable medical devices to provide a disposable sterile sheath as an alternative to sterilizing the device before each use. The disposable sheath covers a predetermined portion of the medical device functioning as a sterile barrier between the individual being examined and the medical device used for such examination. Thus the medical device can be conveniently and repeatedly reused without being in a sterile condition for each use.

For example, disposable sheaths are used on thermometers as shown in U.S. Pat. No. 4,197,944; on catheters as shown in U.S. Pat. No. 4,178,735; on esophageal probes as shown in U.S. Pat. No. 4,349,031; on laryngoscope blades as shown in U.S. Pat. No. 3,426,749 and on endoscopes as shown in U.S. Pat. Nos. 4,991,565 and 4,974,580.

Except for the endoscope sheaths of U.S. Pat. Nos. 4,991,565 and 4,974,580, the previous patents for disposable sheath devices are not used with medical devices that require visual examination through the sheath.

Although the endoscope sheath of U.S. Pat. No. 4,991,565 permits visual examination through the sheath, it does not address the problem of visual acuity through the sheath. The known sheath also supports an air tube, a water tube and a suction tube and is thus a relatively complex and expensive sheath. In addition, the known sheath must be custom-fitted to the endoscope in an elongated groove formed along the barrel of the endoscope.

U.S. Pat. No. 4,974,580 requires a custom fitted sheath having a glass lens and an enlarged mounting structure to engage a body portion of the endoscope that supports a video camera.

It is thus desirable to provide a relatively inexpensive disposable sheath for an endoscope that provides optimum visual acuity through the sheath.

OBJECTS AND SUMMARY OF THE INVENTION

Among the several objects of the invention may be noted the provision of a novel endoscope sheath, a novel disposable endoscope sheath that permits optimum visual acuity through the sheath, a novel disposable endoscope sheath having a lens cover portion that minimizes light reflection into the field of vision of the endoscope, a novel endoscope sheath having a lens cover with an anti-fogging component, a novel cover for an endoscope that encloses the entire endoscope, and a novel method of providing optimum visual acuity through a sheath for an endoscope.

Other objects and features of the invention will be in part apparent and in part pointed out hereinafter.

In accordance with the invention, the sheath for endoscope includes an elongated sleeve of predetermined length having a lens cover portion provided at one end of the sleeve, thus closing the end of the sleeve. The opposite end of the sleeve is open to permit insertion of an endoscope barrel.

In one embodiment of the invention the sleeve can be formed of a rigid material to accommodate the rigid barrel of an endoscope. In another embodiment of the invention the sleeve can be formed of a flexible material to accommodate the flexible barrel of an endoscope.

Whether the sheath is rigid or flexible, the lens cover portion can be joined to the inside of the sheath or the outside of the sheath.

A cap section of the lens cover portion is formed to a predetermined thickness that minimizes the reflection or scattering of light from a light source in the endoscope onto the field of view of the endoscope. The dimensional characteristics of the lens cover portion are thus selected to minimize interference of reflected light with the field of view to provide optimum visual acuity through the sheath.

The lens cover portion of the sheath can be formed or otherwise provided with an anti-fogging component to minimize condensation or accumulation of fluid onto the lens cover portion and thus enhance visual acuity.

The sheath can be formed with lens cover portions that are inclined at predetermined angles to correspond with lens viewing angles of the endoscope.

The sheath also includes means for preventing slippage between the sleeve portion of the sheath and the barrel portion of the endoscope. The slippage prevention means include one or more indentations formed along the length of the sleeve or one or more compressed areas on the sleeve that grip against the inserted endoscope barrel. The sleeve material may be coated or otherwise constituted to enhance friction retention on an endoscope barrel.

The disposable sheath can be incorporated in a disposable cover for covering the entire endoscope as well as the barrel. The cover thus includes a drape portion for covering the main body section of the endoscope and the sheath for enclosing the barrel of the endoscope. The sheath is detachably joinable to the drape portion but can also be integrally formed with the drape portion. The cover also includes a tail section branching away from the main section of the drape portion for enclosing cables such as illumination and/or electric cables that extend from a main body portion of the endoscope.

The invention accordingly comprises the constructions and method hereinafter described, the scope of the invention being indicated in the claims.

DESCRIPTION OF THE DRAWINGS

In the accompanying drawings,

FIG. 1 is a simplified schematic perspective view of a rigid endoscope and a sheath for such endoscope which incorporates one embodiment of the invention, the sheath being shown prior to installation on the endoscope;

FIG. 2 is a view similar to FIG. 1 after assembly of the sheath to the endoscope;

FIG. 3 is a fragmentary detail section view thereof;

FIGS. 3a, 3b, 3c, and 4 are fragmentary detail section views of other embodiments thereof;

FIG. 5 is an exploded perspective view corresponding to the embodiment of FIG. 3a;

FIG. 9 is a simplified schematic view of a sheath and drape for an endoscope;

FIG. 10 is a simplified schematic view showing the endoscope prior to insertion in the drape;

FIG. 11 is a simplified schematic view showing partial assembly of the endoscope into the sheath and drape;

FIG. 12 is a simplified schematic view showing full enclosure of the endoscope within the sheath and drape;

FIG. 13 is a partly exploded enlarged section view thereof prior to insertion of the endoscope;

FIG. 14 is a view similar to FIG. 13 after insertion of the endoscope; and

FIG. 15 is another embodiment thereof.

Corresponding reference characters indicate corresponding parts throughout the several views of the drawings.

DETAILED DESCRIPTION OF THE INVENTION

Figure 6:
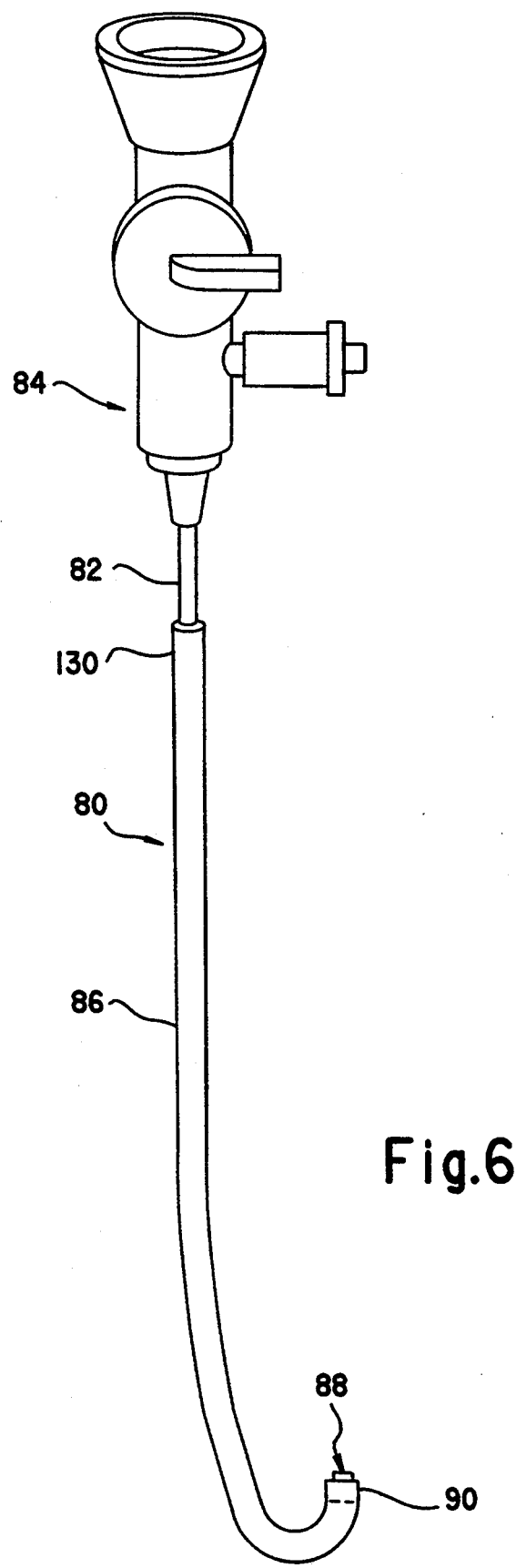
FIG. 6 is a simplified perspective view of a flexible endoscope and a flexible sheath for such endoscope incorporating another embodiment of the invention, the sheath being shown assembled to the flexible endoscope.

A sheath incorporating one embodiment of the invention for use with a rigid endoscope is generally indicated by the reference number 10 in FIG. 1.

Referring to FIGS. 1–3, the sheath 10 comprises a rigid, generally tubular sleeve portion 12 having a cup-shaped lens cover portion 14 provided at one end 16 of the sleeve. An opposite end 18 of the sleeve portion 12 is an open end.

The sleeve 12, which can be extruded or injection molded, is formed of a rigid plastic material such as for example, a spiral wound polyester, polyvinyl chloride (PVC), or an opaque or transparent polycarbonate preferably having a wall thickness of approximately 0.001 to 0.010 inches. The lens cover portion 14 is preferably formed of a clear transparent polycarbonate or PVC having a wall thickness of approximately 0.002 to 0.005 inches. The overall length of the lens cover portion 14 can be approximately 0.25 inches.

Preferably, the lens cover portion 14 is joined to the inside of the sleeve portion 12 as shown in FIG. 3. However, as shown in FIGS. 3a and 5, a diametrically larger cup-shaped lens portion 14a can be joined to the outside of the sleeve portion 12. The lens cover portion 14 and the sleeve portion 12 can be heat sealed or otherwise suitably bonded together in a known manner using a solvent or adhesive or other known joining process depending upon the material constituents of the components 12 and 14. As a further option the lens cover portion can be formed as a disc 15 and butt sealed to the end 16 of the sleeve 12 as shown in FIG. 3c. The sheath can also be constructed as a single piece unit by means of injection molding, compression molding or other suitable known forming process.

A known endoscope on which the sheath 10 is used is generally indicated by the reference number 20 in FIG. 1. The endoscope 20 provides telescopic vision and suitable illumination but does not include irrigation, air or suction channels. An ocular portion 22 of the endoscope 20, which includes an eyepiece 24, is joined to a main body or telescope portion 26. A light source connector 28 branches away from the main body portion 26 and an elongated barrel 30 of the endoscope that is substantially coaxial with the ocular portion 22 extends from the main body portion 26.

Depending upon the type of endoscope selected, the barrel 30 can have a diametrical range of approximately 1.7 mm. to 11 mm. and the sheath 10 is sized to suitably accommodate a specific barrel diameter, with a minimum radial clearance from the barrel 30 that permits convenient insertion and removal of the endoscope barrel.

Figure 7:
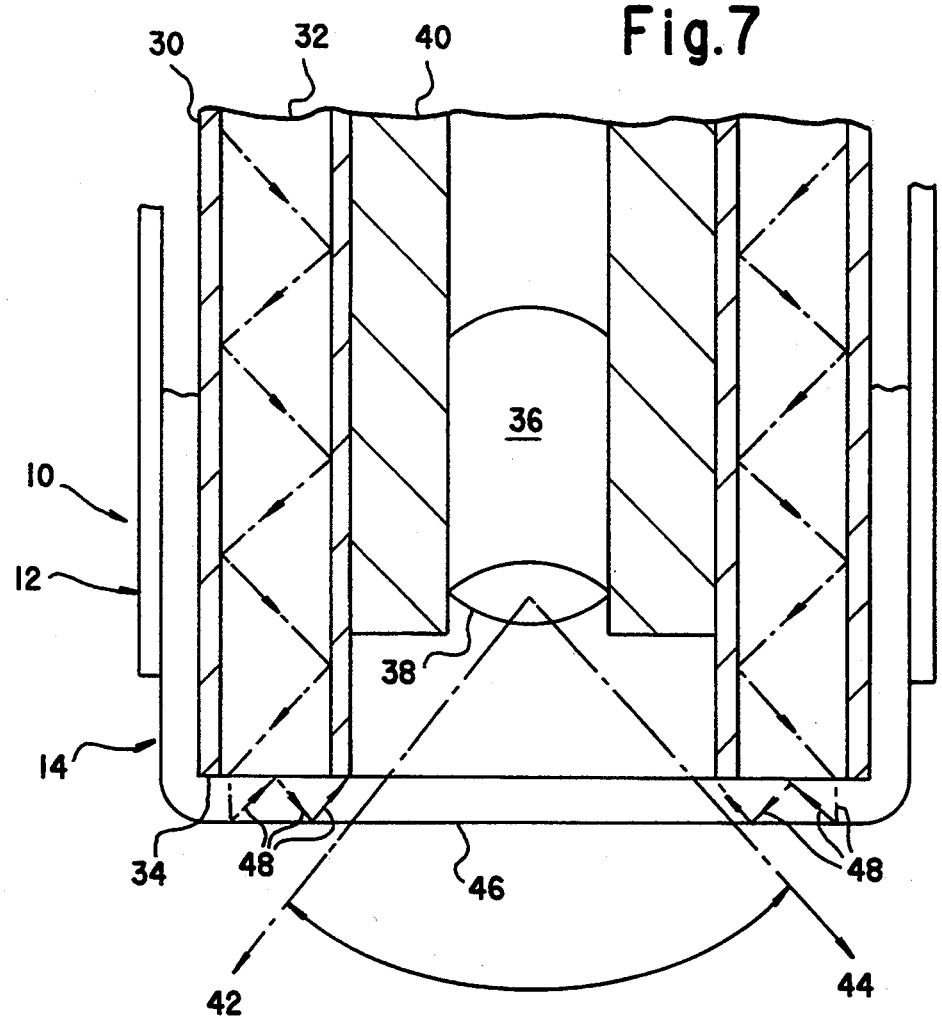
FIG. 7 is an enlarged schematic section view of an end portion of an endoscope within a sheath showing light ray reflection therein, corresponding to the embodiments of FIGS. 1–3 and 6.
Figure 8:
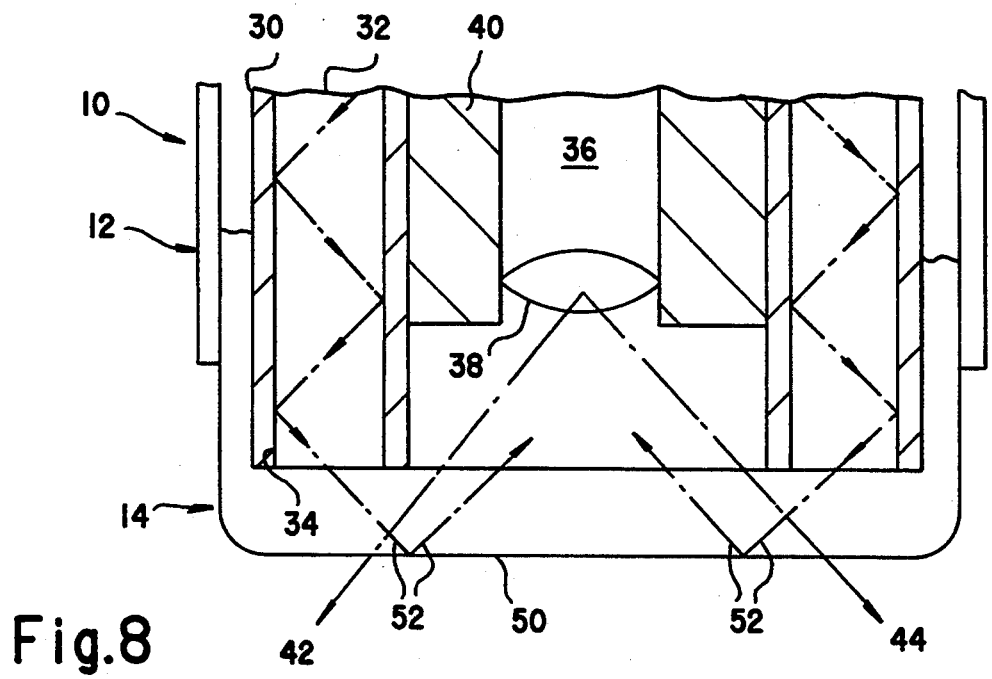
FIG. 8 is a view similar to FIG. 7 showing the light reflection characteristics for an endoscope sheath having a lens cover of greater thickness than that shown in FIG. 6.

Referring to FIGS. 7 and 8, the barrel 30 includes an annular light channel 32 which transmits light from optic fibers (not shown) to an end 34 of the barrel 30. A rod lens arrangement 36 which leads to a focal lens 38 is typically supported concentrically of the light channel 32 in any suitable known manner as by a lens support structure 40 within the barrel 30. Under this arrangement, a field of view indicated by the arrows 42 and 44 is provided at the open end 34 (FIG. 7).

The lens cover portion 14, which can be vacuum or thermo formed, includes a cap section 46 through which the field of view 42, 44 is taken. As shown in FIG. 7, reflected light rays 48 from the light channel 32 transmitted into the cap section 46 do not reflect into the field of view 42, 44 and consequently do not interfere with the field of view. Optimum visual acuity is thus provided through the cap section 46 from the focal lens 38.

It has been found that cap section thicknesses in excess of 0.010 inches as indicated by the reference number 50 in FIG. 8, may reflect light into the field of view 42, 44 as shown by the light rays 52, and consequently interfere with the field of view. Less than optimum visual acuity is thus provided through an excessively thick cap section 50 from the focal lens 38.

The endoscope sheath 10 can be made in any selected length and need not extend the full length of the barrel 30. Preferably the sheath 10 should be of sufficient length to cover a predetermined length of the barrel 30 that penetrates a body cavity and also cover a portion of the barrel 30 that extends outwardly from the body cavity. A sheath 10 having a length of approximately 4⅞" to 6⅜" has been found suitable for most purposes. Thus, the sheath 10 is of adequate length even if it covers only a portion of the barrel 30 as shown in FIG. 2.

To help ensure retention of the sheath 10 on the barrel 30, the sheath at mid-length, for example, can be compressed slightly from opposite sides of the sleeve 12 to form a gradual indentation 54 (FIG. 2). If desired the indentation 54 can be preformed. The indentation 54, in addition to ensuring against slippage of the sheath 10 relative to the barrel 30, also assures that the lens cover portion 14 remains in position at the end 34 of the barrel 30. The anti-slip feature provided by the indentation 54 also assures that the sheath 10 stays on the barrel 30 when the endoscope is removed from a body cavity such as a nostril. The anti-slip feature can also be provided by a reduced inner diameter at one or more locations on the sheath 10 and/or by using a material with a relatively high internal friction surface.

It has been found that use of an endoscope 20 occasionally results in fogging of the lens 38 due to differences in temperature between the endoscope and the environment in which the endoscope is disposed for medical examination. Fogging usually occurs when the lens 38 and the end portion 34 of the barrel 30 are cold enough to condense moisture in the immediate vicinity of view, such as when an endoscope is at room temperature (i.e., 68° F.) and is placed in the vicinity of warm moist tissue. The relatively large metallic mass of the endoscope barrel 30 keeps the endoscope lens 38 at a cool temperature for an extended period of time even though the endoscope is in contact with warm surroundings during examination.

The sheath 10 provides thermal insulation that creates a desirable thermal gradient between the endoscope lens 38 and the endoscope lens cover portion 14. The endoscope lens cover portion 14 can thus be warmed by the body relatively quickly to the temperature of the viewing surroundings. The warm surface of the sheath 10 does not readily condense moisture and thereby helps provide a fog-free view through the lens cover portion 14. The sheath 10 thus provides an anti-fog capability. The thermal gradient feature also improves patient comfort by preventing contact of a relatively cold endoscope barrel 30 with the patient.

Fog free operation can also be enhanced by application of a known anti-fog component (not shown) in the resin used to form the lens cover portion 14, or onto the cap section 46 during manufacture. The anti-fog component can be a surfactant or polymer or corona treatment or other means by which a hydrophyllic surface is created to disperse water micro-droplets that might condense on the cap section 46. The anti-fog treatment is also capable of dispersing fluids that come in contact with the cap section 46 of the lens cover portion 14 such as saliva or other body secretions, in order to minimize droplet formation on the cap section 46 that would otherwise interfere with a view through the lens cover portion 14.

Another embodiment of a sheath for an endoscope is generally indicated by the reference number 60 in FIG. 4. The endoscope sheath 60 includes a sleeve portion 62 and a lens cover portion 64 having a cap section 66. The cap section 66 is oriented at an angle of approximately 60° relative to a central axis 68 of the cover portion 64. Other orientation angles such as within the range of 0° to 90° are feasible. The lens cover portion 64 is joined to the outside of the sleeve 62. The sheath 60 is otherwise similar to the sheath 10.

If desired, an alternate smaller diameter lens cover portion (not shown) corresponding to the lens cover portion 64 can be joined to the inside of the sleeve 62, in the manner shown in FIG. 3. The sheath 60 is used in a manner similar to that previously described for the sheath 10.

Another embodiment of a sheath for an endoscope is generally indicated by the reference number 80 in FIG. 6. The sheath 80, which is a flexible sheath, is fitted onto a flexible barrel 82 of an endoscope 84. The sheath 80 includes a flexible sleeve portion 86 with a lens cover portion 88 which can be identical to the lens cover portion 14, joined to an end 90 of the sleeve portion 86.

The sleeve portion 86 can be formed of a suitable known flexible polymer or polypropylene material having a wall thickness of approximately 0.001 to 0.012 inches.

The lens cover portion 88 is joined to the inside of the sleeve portion 86 in a manner similar to that shown in FIG. 3. If desired, an alternate diametrically larger lens cover portion (not shown) can be joined to the outside of the sleeve portion 86 in the manner shown in FIGS. 3a and 5. The lens cover portion 88 is joined to the sleeve portion 86 by heat sealing or any other suitable known bonding method. The lens may also be in the form of a disc 15, as shown in FIG. 3c, bonded to the end 90 of the sleeve 86.

The sheath 80 is sized to provide a minimum radial clearance from the barrel 82 that permits convenient insertion and removal of the endoscope barrel.

Whether the lens cover portion is joined to the inside or outside or end of a flexible sleeve, it has been found beneficial to form reduced diametrical sections on the sleeve to prevent slippage of the sleeve with respect to the barrel 82. For example, a reduced diametrical section such as at an indentation 92, is shown in FIG. 3b. The indentation 92 can be formed around the entire circumference of the sleeve 86 and a plurality of such indentations 92 can be staggered along the length of the sleeve at predetermined intervals.

As an alternative or addition to the indentations 92, an indentation such as 94 (FIG. 3b) can be provided in the sleeve 86. The indentation 94 need not extend all the way around the sleeve and can have, for example, a 0° to 360° extent. Other longitudinally spaced indentations such as 96 which is offset 180° from the indentation 94 can also be provided. Thus an alternate pattern of indentations 94 and 96 can be provided at predetermined intervals along the length of the sleeve 86.

The sleeve 86 can be applied to the endoscope barrel 82 in a manner similar to that used to apply a stocking to a person's foot. The end of the endoscope barrel 82 is thus directed into the sheath 80 to engage the lens cover portion 88. The sleeve 86 is then extended along the barrel 82 to the full length of the sheath 80. When an endoscopic examination is completed, the sleeve 86 can be peeled away from the barrel 82 in the same manner that a stocking is removed from a person's foot.

Since barrels 82 of different endoscopes 84 may have different diameters, the flexible sleeve portion 86 of the sheath 80 can likewise be formed in different diametrical sizes to accommodate the different sized barrels.

As previously discussed for the rigid sheath 10, the flexible sheath 80 can have a length of approximately $4\frac{7}{8}$ inches to $6\frac{7}{8}$ inches and need not extend the full length of the barrel 82 as shown in FIG. 6.

In some instances it may be desirable to cover the entire endoscope to provide a complete sterile barrier between the endoscope and the patient being examined. Thus, a cover for an endoscope, which incorporates a further embodiment of the invention, is generally indicated by the reference number 100 in FIGS. 9–12. The cover 100 includes a drape portion 102 and a sheath 104 (FIGS. 11 and 12) substantially identical to the sheath 10.

Referring to FIG. 9, the drape portion 102 includes a main body cover section 106 and a tail section 108 extending from the main body section 106. The main body section 106 and the tail section 108 are preferably formed of a polyethylene film.

An ocular engaging member 110, in the form of an annulus, is joined to the main body cover section 106 at an end 112 and an elongated annular sheath grip 114 is joined to the main body cover section 106 at an end 116. The ocular engaging member 110 and the sheath grip 114 are preferably formed of a soft deformable foam material such as medium density closed cell polyethylene or an elastomer.

Referring to FIG. 13, the ocular engaging member 110 includes opposite base ends 118 and 120. The main body cover section 106 can be joined to the base end 120 as shown in FIG. 13 or the base end 118 as shown in FIG. 15.

In using the cover 100, the tail section 108 is collapsed toward the main body cover section 106 as shown in FIG. 10. The barrel 30 of a rigid endoscope 20 is directed through the tail portion 108 into the sheath grip 114 as shown in FIG. 11. The main body 26 of the endoscope 20 is thus disposed in the main body cover section 106 and the rigid barrel 30 projects from the sheath grip 114.

The ocular engaging member 110 can then be fitted onto the ocular portion 22 of the endoscope 20 in the manner shown in FIGS. 12 and 14 such that the eyepiece 24 is substantially flush with the base end 118 of the ocular engaging member 110. The ocular engaging member 110 is sized to snugly embrace yet be detachable from the ocular portion 22. The tail section 108 is extended along the light source connector 28 and the optic fiber cables 122 that extend from the light source connector 28. The tail section can also be used to accommodate other cables such as video cables (not shown) if a camera is used with the endoscope.

The sheath 104 is fitted onto the barrel 30 such that the lens cover portion 14 (FIG. 11) engages the end 34 of the barrel 30. The end 18 of the sheath 104 is inserted into the sheath grip 114 (FIGS. 12 and 14). The sheath grip 114 is sized to snugly embrace the end 18 of the sheath 104 yet permit detachment of the sheath 104 from the sheath grip 114. If desired, the sheath grip 114 can include a reduced internal diameter section to enhance the grip. The sheath 104 and the sheath grip 114 are thus of sufficient length to mutually engage after the sheath 104 has accommodated the barrel 30.

The tail section 108 of the drape portion 102 can be secured around the optic fiber cable 122 using adhesive straps 124 individually spaced from each other as shown in FIGS. 12 and 14. As an alternative to the adhesive straps 124, a single ribbon 126 can be joined to the main body section 106 as shown in FIGS. 11 and 12 and coiled around the tail section 108 in the manner shown in FIG. 12. An end 128 of the ribbon 126 can be adhesively secured to a corresponding end of the tail section 108.

With the endoscope 20 thus covered by the cover 100, the only portion of the endoscope that is exposed to the outside environment is the eyepiece 24 of the ocular portion 22. Such exposure can also be eliminated by providing a clear cover 132 (FIG. 13) adhered to the base 118 of the ocular engaging member 110. The cover 132 can remain in place during viewing or removed for a direct view through the eyepiece 24.

If desired, the sheath 104 can be pre-bonded to the sheath grip 114 such that the cover 100 and the sheath 104 constitute a preassembled unified structure.

It should be noted that a flexible sheath such as the sheath 80 can replace the rigid sheath 104 in the cover 100. For example, the flexible sheath 80 can be pre-bonded to the sheath grip 114 (not shown). As a further option, a small rigid length of sheath material (not shown) can be joined to an end 130 (FIG. 6) of the flexible sleeve 86 to permit manual assembly of the flexible sheath 80 to the sheath grip 114 in the same manner that the rigid sheath 104 is inserted into the sheath grip 114.

Some advantages of the present invention evident from the foregoing description include a disposable sheath that provides optimum visual acuity for use with an endoscope or other similar device. A further advantage is the anti-fogging capability of the lens cover portion of the sheath, which helps assure optimum visual acuity. The sheath is easy to install onto or remove from an endoscope and can thus be immediately installed prior to use of the endoscope. Still another advantage is that the sheath can be incorporated in a disposable cover that covers the entire endoscope. A still further advantage is that depending upon the material used to constitute the sheath, the invention is applicable to rigid as well as flexible endoscopes. Still another advantage is the ability to view through the wall of the sleeve when the sleeve is made of clear material. This view is accomplished by drawing the endoscope back from its fully inserted position. Such use allows a rapid view of long contiguous areas. Partial retraction of the endoscope from the sheath tip also allows a wider view of tissue in contact with the sheath tip. Such perspectives are not obtainable with an unsheathed endoscope and provide unique opportunities in observation of such tissues.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A disposable sheath for an endoscope having an elongated barrel comprising, a) a preformed elongated disposable sleeve of generally circular cross-section having a predetermined length and diameter for detachably fitting onto and accompanying an endoscope barrel, said sleeve including means for preventing slippage of said sleeve relative to said barrel once said sleeve is disposed on said barrel comprising a reduced diameter section of said sleeve, b) a preformed transparent lens cover secured at one end of said disposable sleeve to permit a field of view from the endoscope through said lens cover, said lens cover being without any apertures, and c) said lens cover having a substantially planar section with a predetermined central portion through which said field of view is taken and a predetermined peripheral portion surrounding said predetermined central portion, said planar section being non-collapsible and of a predetermined thickness such that light reflected through the predetermined peripheral portion of the planar section from the endoscope does not reflect through the predetermined central portion so as to interfere with the field of view through said planar section.

2. A disposable sheath as claimed in claim 1 wherein said sleeve has an elongated axis and the reduced diameter section includes an indentation in said sleeve projecting toward said axis.

3. A disposable sheath as claimed in claim 2 wherein said indentation has a predetermined radial extent with respect to said axis.

4. A disposable sheath as claimed in claim 3 including more than one said indentation and wherein said indentations have a predetermined axial extent and are staggered lengthwise along said sleeve at predetermined intervals.

5. A disposable sheath as claimed in claim 2 wherein said radial extent is in the range of 0° to 360°.

6. A disposable sheath as claimed in claim 1 wherein said lens cover is cup shaped and has an annular wall with said planar section forming a closed end of said annular wall.

7. A disposable sheath as claimed in claim 6 wherein the annular wall of said lens cover is joined to the inside of said cup shaped sleeve.

8. A disposable sheath as claimed in claim 6 wherein the annular wall of said lens cover is joined to the outside of said cup shaped sleeve.

9. A disposable sheath as claimed in claim 6 wherein said cup-shaped lens cover has a central axis and said planar section is oriented at a predetermined angle with respect to said central axis.

10. A disposable sheath as claimed in claim 9 wherein said planar section is oriented in the range of 0° to 90° with respect to said central axis.

11. A disposable sheath as claimed in claim 1 wherein said sleeve is substantially rigid.

12. A disposable sheath as claimed in claim 1 wherein said sleeve is formed of a substantially flexible material.

13. A disposable sheath as claimed in claim 1 wherein said lens cover planar section has a thickness in the range of about 0.002 inches to 0.010 inches.

14. A disposable sheath as claimed in claim 1 wherein said lens cover has a fog-free additive to disperse or prevent condensation of fluid on said lens cover.

15. A method for providing optimum visual acuity in a disposable sheath for an endoscope having a field of view and comprising,
 a) forming a non-collapsible lens cover from an optically clear transparent plastic material with a substantially planar section without apertures, said lens cover having a predetermined central portion through which said field of view is taken and a predetermined peripheral portion surrounding said predetermined central portion, said planar section being of a predetermined thickness such that light reflected through the predetermined peripheral portion of the planar section from the endoscope does not reflect through the predetermined central portion so as to interfere with the field of view through said planar section,
 b) limiting the thickness of the planar section of the formed lens cover to a range of about 0.002 inches to 0.010 inches, such that light reflected through the planar section from an endoscope does not interfere with the field of view through the planar section, and
 c) securing the lens cover with planar section at one end of a disposable tubular sleeve member that is sized to slidably fit onto a endoscope barrel such that the planar section is adjacent the field of view end of the endoscope and at least a portion of the sleeve member tightly engages said endoscope.

16. The method of claim 15, including the step of reducing the diameter of the tubular sleeve member at one or more predetermined locations along the length of the sleeve.

17. The method of claim 15 including combining an antifogging component with the planar section.

* * * * *